US011145392B2

(12) United States Patent
Pollack et al.

(10) Patent No.: US 11,145,392 B2
(45) Date of Patent: Oct. 12, 2021

(54) SINGLE POINT CHAIN OF CUSTODY WITHIN A DISTRIBUTED AUTOMATION PLATFORM

(71) Applicant: Siemens Healthcare Diagnostics Inc., Tarrytown, NY (US)

(72) Inventors: Benjamin S. Pollack, Jersey City, NJ (US); Colin Mellars, Tucson, AZ (US); Baris Yagci, Montclair, NJ (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 369 days.

(21) Appl. No.: 16/319,270

(22) PCT Filed: Jul. 19, 2017

(86) PCT No.: PCT/US2017/042926
§ 371 (c)(1),
(2) Date: Jan. 18, 2019

(87) PCT Pub. No.: WO2018/017757
PCT Pub. Date: Jan. 25, 2018

(65) Prior Publication Data
US 2019/0228846 A1 Jul. 25, 2019

Related U.S. Application Data

(60) Provisional application No. 62/365,268, filed on Jul. 21, 2016.

(51) Int. Cl.
G16H 10/40 (2018.01)
G01N 35/00 (2006.01)
(Continued)

(52) U.S. Cl.
CPC ......... G16H 10/40 (2018.01); G01N 35/0095 (2013.01); G01N 35/00732 (2013.01);
(Continued)

(58) Field of Classification Search
CPC ....... G01N 35/0095; G01N 2035/0406; G01N 2035/00752; G01N 2035/0326;
(Continued)

(56) References Cited

U.S. PATENT DOCUMENTS 6,299,567 B1 * 10/2001 Forrest ................. B01F 9/0018
366/220
6,335,166 B1 * 1/2002 Ammann .............. B01F 9/0001
435/6.11
(Continued)

FOREIGN PATENT DOCUMENTS

| JP | 2004-525376 A | 8/2004 |
| JP | 2015-075343 A | 4/2015 |
| WO | 02/086514 A2 | 10/2002 |

OTHER PUBLICATIONS

PCT International Search Report and Written Opinion dated Sep. 29, 2017 (8 Pages).

Primary Examiner — Shogo Sasaki

(57) ABSTRACT

Embodiments are directed to a combination of an automation system that continuously tracks the identity and positions of all of its pucks with a single sample identification station and covers/interlocks in order to provide sample chain of custody without the need to re-identify the sample at points of interaction (aspiration, de-capping, etc.). This eliminates the need to have sample identification stations at each interaction point. This reduction of hardware allows the system to be cheaper, smaller, and more reliable. It also allows not only the automation system, but also existing pre-analytical/analytical equipment connected to the automation system, to run more efficiently.

19 Claims, 7 Drawing Sheets

(51) Int. Cl.
*G16H 40/40* (2018.01)
*G01N 35/04* (2006.01)

(52) U.S. Cl.
CPC ... *G16H 40/40* (2018.01); *G01N 2035/00326* (2013.01); *G01N 2035/00752* (2013.01); *G01N 2035/00801* (2013.01); *G01N 2035/0406* (2013.01)

(58) Field of Classification Search
CPC ... G01N 35/00732; G01N 2035/00801; G16H 40/40; G16H 10/40
See application file for complete search history.

(56) References Cited

U.S. PATENT DOCUMENTS

| | | | |
|---|---|---|---|
| 6,426,043 B1* | 7/2002 | Cohen | G01N 35/04 422/63 |
| 2003/0044323 A1* | 3/2003 | Diamond | B01L 9/06 422/562 |
| 2008/0190735 A1 | 8/2008 | Luoma | |
| 2008/0231452 A1 | 9/2008 | Levin | |
| 2015/0079695 A1 | 3/2015 | Pollack et al. | |
| 2015/0338427 A1 | 11/2015 | Pollack et al. | |

* cited by examiner

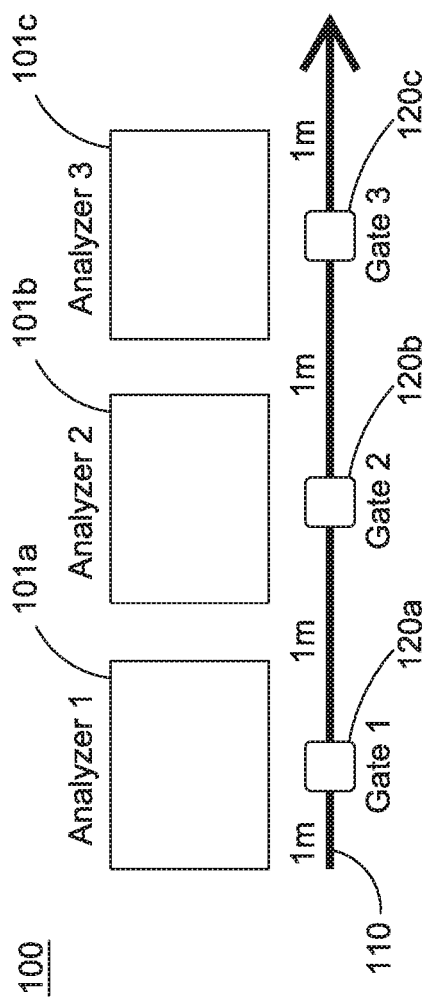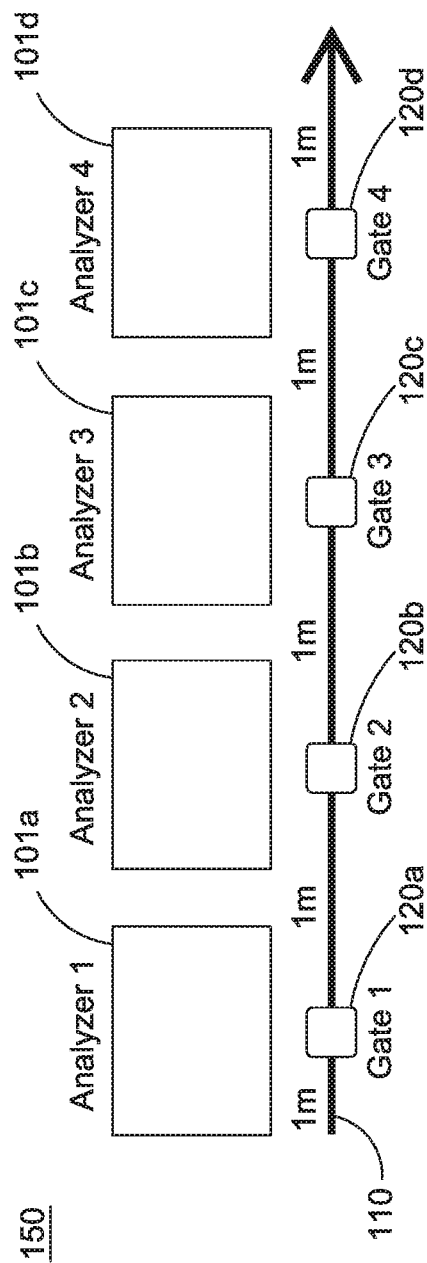
FIG. 1A
FIG. 1B

| Configuration | Effective Capacity | Analytical Capacity | Realized Capacity |
|---|---|---|---|
| 3 Analyzer Baseline | 77.7 sph | 675 sph | 11.5% |
| 4 Analyzer Baseline | 66.05 sph | 900 sph | 7.3% |
| 3 Analyzer Next Gen | 200.0 sph | 675 sph | 29.6% |
| 4 Analyzer Next Gen | 194.6 sph | 900 sph | 21.6% |

FIG. 2

Effective Throughput per Configuration

| | 1 | 2 | 3 | 4 |
|---|---|---|---|---|
| Baseline | 120.2 sph | 94.4 sph | 77.7 sph | 66.1 sph |
| Next Gen | 211.8 sph | 205.71 sph | 200 sph | 194.59 sph |

Effective Utilization of Analytical Capacity

| | 1 | 2 | 3 | 4 |
|---|---|---|---|---|
| Baseline | 53.4% | 20.1% | 11.5% | 7.3% |
| Next Gen | 94.1% | 48.4% | 29.6% | 21.6% |

SINGLE POINT CHAIN OF CUSTODY WITHIN A DISTRIBUTED AUTOMATION PLATFORM

CROSS-REFERENCE TO RELATED APPLICATIONS

This application claims priority to U.S. Provisional Patent Application No. 62/365,268 filed on Jul. 21, 2016, the contents of which are herein incorporated by reference in their entirety.

TECHNOLOGY FIELD

The present invention relates generally to a distributed automation platform and, more particularly, to interfacing systems within a distributed automation platform.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical analyzers (analyzers or analyzer modules) onto which fluid containers, such as tubes or vials, containing patient samples, have been loaded. The analyzer extracts a liquid sample from sample vessels and combines the sample with various reagents in special reaction cuvettes or tubes. Automated clinical analyzers may include clinical chemistry analyzers, automated immunoassay analyzers, or any other type of IVD testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample.

Traditional approaches to laboratory automation create a situation in which additional systems (e.g., modules) added into a distributed architecture are unable to leverage their available resources and capacity, resulting in a rapidly diminishing return for end users.

Thus, there is a need to provide a more consistent, realizable capacity solution when interfacing systems within a distributed automation solution.

SUMMARY

Embodiments are directed to a distributed automation system comprising a plurality of interconnected modules in an in vitro diagnostics (IVD) environment in a hospital or laboratory setting and to a method of utilizing the same.

According to an embodiment, a distributed automation system for use in an in vitro diagnostics (IVD) environment comprises: a plurality of interconnected modules; an automation track alongside and connected to the plurality of interconnected modules, along which a plurality of carriers move, the plurality of carriers transporting and delivering one or more vessels, each containing a respective sample, between the plurality of interconnected modules; a single acquisition point at a portion of the automation track for acquiring an identification of each of the vessels and each of the carriers by a barcode reader; a cover set over areas of travel and destinations for the samples; and a processor configured to monitor the identification and a location of each of the vessels and each of the carriers and to detect if the cover is breached.

In an embodiment, if a detection occurs indicating the cover is breached, the respective carriers and vessels are rerouted to the single acquisition point. According to an embodiment, the system may further comprise a plurality of cover sensors, each associated with a portion of the cover and configured to send a signal to the processor upon the respective portion of the cover being breached. In an embodiment, upon the respective carriers and vessels being rerouted to the single acquisition point, a reacquisition of the identification of each of the vessels and each of the carriers is obtained.

According to an embodiment, a plurality of track sensors are embedded in the track, the track sensors configured to sense a position of the plurality of carriers and communicate the sensed position to the processor.

In an embodiment, each of the plurality of carriers and the vessels comprise a label assigning each a unique identification code. In an embodiment, the barcode reader reads each of the unique identification codes for the acquiring of the identification of each of the vessels and each of the carriers.

According to an embodiment, a throughput of the system is based on delays incurred at each of the plurality of interconnected modules and along track segments of the automation track.

According to an embodiment, the system further comprises a series of interconnected sample distribution points of clusters of additional systems.

In an embodiment, the cover is (i) set over all areas of the track, (ii) set over a majority portion of the track, or (iii) set over a minority portion of the track.

According to an embodiment, a method of utilizing a distributed automation system for use in an in vitro diagnostics (IVD) environment comprises: providing a plurality of interconnected modules; providing an automation track alongside and connected to the plurality of interconnected modules, along which a plurality of carriers move, the plurality of carriers transporting and delivering one or more vessels, each containing a respective sample, between the plurality of interconnected modules; providing a cover set over areas of travel and destinations for the samples; acquiring, at a single acquisition point at a portion of the automation track, an identification of each of the vessels and each of the carriers by a barcode reader; monitoring, by a processor, the identification and a location of each of the vessels and each of the carriers; and detecting, by the processor, if the cover is breached.

Additional features and advantages are apparent from the following detailed description that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIGS. 1A and 1B are diagrams illustrating exemplary track systems for comparison, according to embodiments provided herein;

FIG. 2 is a table providing capacity comparisons for a plurality of systems, according to embodiments provided herein;

FIGS. 3A and 3B are tables providing throughput and utilization comparisons, respectively, for a plurality of systems, according to embodiments provided herein.

DETAILED DESCRIPTION

Figure 4:
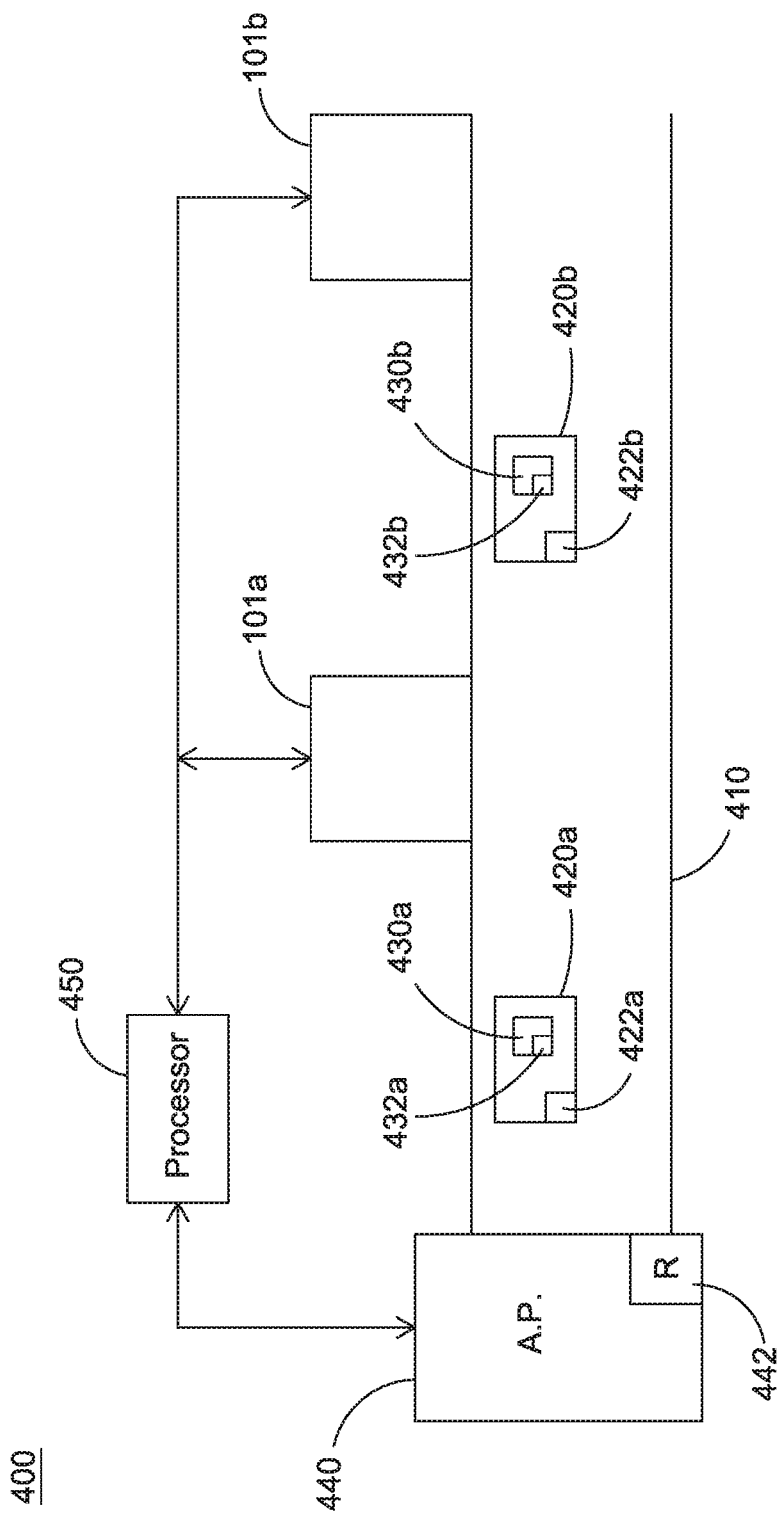
FIG. 4 is a block diagram representation of a distributed automation system, according to embodiments provided herein.

Embodiments are directed to providing a more consistent, realizable capacity solution when interfacing systems (e.g., modules) within a distributed automation solution in an in vitro diagnostics (IVD) environment in a hospital or laboratory setting. A basic system may be defined as a series of interconnected modules that represent a serial collection of processing stations, which introduce a time delay per station due to the processing of one or more sample tubes. In some traditional approaches, an acquisition of a sample identification is provided at every decision point within a distributed system, thus avoiding the need to provide active guarantees around the chain of custody by acquiring information about the tube and the necessary action (e.g., movement, direction, etc.) at any decision point. However, such conventional approaches incur additional time delays by requiring the acquisition information at ever decision point. Moreover, this conventional approach requires additional hardware to be placed at every decision point to obtain the information (e.g., the sample identification). Finally, there is no guarantee around the chain of custody in such a conventional system.

According to embodiments herein, to address the noted deficiencies with the conventional systems, four features that facilitate addressing the issue of providing a more consistent, realizable capacity solution include the following:

1. A single point for the acquisition of the sample identification (e.g., a barcode reader), which pairs a tube's unique ID to the unique ID of a sample carrier (also referred to as a puck) on the automation track;
2. An automation track that is able to continuously keep track of the identity and position of all of its pucks (via various sensors as described herein);
3. A continuous cover set over all or portions of the areas of travel and destinations for the samples; and
4. The ability to detect if any cover has been breached (via various sensors as described herein).

The first and second features allow the system to maintain continuous chain of custody of all samples on the automation system with a single sample identification station (such as a barcode reader), as long as the operator does not manually override the pairing between the tube's ID and the puck's ID (e.g., by reaching into the track and manually replacing one tube with another). The third and fourth features allow the system to detect if the operator ever had the opportunity to perform a manual override. If a puck ever passes through a section of track where the cover interlocks are breached, the chain of custody has been lost and the system assumes that a manual swapping of the tube has or may have occurred (conservative/worst-case-safe design). In this case, the puck is rerouted to the single sample identification station, so chain of custody can be reestablished.

According to embodiments, a combination of an automation system that continuously tracks the identity and positions of all of its pucks with a single sample identification station and covers/interlocks in order to provide sample chain of custody without the need to re-identify the sample at points of interaction (aspiration, de-capping, etc.) is provided. This eliminates the need to have sample identification stations at each interaction point. This reduction of hardware allows the system to be cheaper, smaller, and more reliable. It also allows not only the automation system, but also existing pre-analytical/analytical equipment connected to the automation system to run more efficiently. The improvement in overall system throughput is significant, as further described herein.

Based on the traditional, interconnected system, the equations to determine the average throughput rate are as follows:

$$\Delta t_{sample} = \Delta t_{input} + \Delta t_{preanalytics} + \Delta t_{analytics} \qquad (1); \text{ and}$$

$$\text{Throughput} = (\Delta t_{sample})^{-1} * 3600 \qquad (2).$$

Equation (1) above requires all units to be in seconds per sample, and Equation (2) requires $\Delta t_{sample}$ to be seconds per sample. The result is the throughput in samples per hour.

Example systems under consideration are shown in FIGS. 1A and 1B, which are diagrams 100, 150 illustrating exemplary track systems for comparison. As shown, FIG. 1A includes three analyzers 101a, 101b, 101c, while FIG. 1B includes four analyzers 101a, 101b, 101c, 101d. Each analyzer 101 has a corresponding gate 120 to divert pucks to the instrument and one meter of track 110 between them. The individual rates of the devices that will be used in the time delay calculation are as follows:

Interface Gate Throughput is 1,500 samples/hr;
Track Speed is 173 mm/sec;
Track Distance between gates is 1 m;
Analyzer throughput rate is 225 samples/hr (1800 tests/hr and 8 tests per sample).

The track is assumed to be in steady state (constant flow of uninterrupted pucks through the segment), and the flow is linear, meaning that pucks pass all the way though the segment in consideration.

Using the information provided in the previous section, the contributors to the delays to be computed are for the gates 120, analyzers 101, and the track segments 110. Because of the assumption that the track is a linear arrangement, the following is the equation to calculate the total time delay experienced by each sample (on average):

$$T_{sample} = \Sigma t_{track} + \Sigma t_{gates} + (1/N_{analyzers}) * \Sigma t_{analyzers} \qquad (3).$$

For the three analyzer configuration 100 shown in FIG. 1A, the inputs for the above equation are 23.1 s for the track, 7.2 s for the gates, and 16s for the analyzer, which results in a total time delay of 46.3 s, or an effective throughput of 77.7 samples per hour in the three system configuration 100.

By adding in the fourth analyzer 101d, additional gate 120d, and two additional meters of track 110 in the four analyzer configuration 150 of FIG. 1B, and fulfilling the same equation, the following are the inputs for the equation: 28.9 s for the track, 9.6 s for the gates, and 16s for the analyzer, with the result being a total time delay of 54.5 s, or an effective throughput of 66.1 samples per hour (sph).

According to embodiments herein, a distributed automation platform optimizes two key characteristics in the equation above: (1) reducing the time to travel on the track, and (2) eliminating the penalty for stopping at a gate by eliminating this operation. To accomplish the first, the track speed is set at 2 m/s, and the gate delay is set to 0 s. Incorporating the track speed adjustment for the three analyzer system results in, according to embodiments provided herein, a track travel delay of 2 s versus the 23.1 s and 2.5 s versus 28.9 s for the four analyzer scenario. Using this in the above equation, the results are as follows:

3 analyzer system→18.0s delay or 200 sph
4 analyzer system→18.5s delay or 194.5 sph Examining the results of the two scenarios and two different systems, several important elements are apparent. The throughput of the analyzers is the average throughput of all of the analyzers attached, which, in this case, is 16 s (or 225 samples per hour based on the assumptions). This suggests that the throughput rates of analytical systems interfaced in automation need to be advanced collectively to realize maximum benefit, and that either local optimizations or slow replacements of analyzers will produce little or no net effect on the system. As a further example, if one of the systems in this analysis is replaced with a system that is twice as fast, the overall net improvement will only be 2.66 s on the average delay of the samples in steady state. As the number of analyzers in a given segment increases, this effect is further diluted and dominated by the slower systems.

The next key aspect of the operation of this system is the influence of the distance and speed of the track system. For each of the systems, the travel speed of 173 mm/s accounts for the majority of the delay in the overall steady state calculation. By improving the speed performance of the track system, a significant improvement in the performance of the system can be realized. In the example, by increasing the track speed by 10 fold, the effective throughput rate is approximately a 2× improvement in the overall throughput performance of the system (e.g., for the 3 analyzer system, the effective rate would be 141 samples per hour versus 77.7 samples per hour).

The final aspect for consideration is the elimination of the gate reading penalty. By needing, in traditional systems, to reacquire the sample ID at each decision point (gate) and determine what action to take or not take, there is a constant penalty applied to the processing of the sample, which is exacerbated the larger the system becomes. In the examples given herein for traditional systems, there is a 2.4 s*Ngates penalty applied to the sample to just progress to each location, make this determination, and progress. In this example, two-thirds of this time is wasted as the decision if the tube should continue to progress. By eliminating this penalty in the system, with all other things being held constant, the improvement for the three analyzer system according to embodiments provided herein would be an effective throughput of 106.5 samples per hour versus the 77.7 samples per hour rate in the baseline (traditional) system.

As a side effect of the comparisons between the systems, another interesting result appears in terms of the effective capacity of the system compared with the realized capacity of the system. For each of the scenarios observed, their effective capacities are shown in the table 200 of FIG. 2 (where "Baseline" refers to traditional systems and "Next Gen" refers to the distributed automation platform according to embodiments described herein).

The result of this examination shows that the deployed analytical capacity is being significantly underutilized in the baseline configuration with the additional analyzer providing significantly diminishing returns, whereas, in the next generation concept, the same diminishing returns are seen when moving from three to four analyzers (the effective utilization of the analytical capacity is substantially higher). This more effective use of analytical capacity represents a much higher return on investment for the customer who has purchased these analytical systems.

Extending the analysis further, and examining from one system through four systems the effective throughputs and analytical capacity utilization, the results are shown in the tables 300 and 350 of FIGS. 3A and 3B, respectively.

As can be seen from the results, the next generation system represents nearly constant system throughput, while the traditional interconnected automation system represents a significant decay in the utilization of available resources. While neither system is maximizing the use of available analytical capacity as configurations get significantly larger, the next generation system has significantly higher utilization of available resources in smaller configurations.

Based on the information and analysis presented, several important conclusions can be drawn from this basic modeling approach. The first is, in the traditional interconnected automation solutions, there is a significant underutilization of available analytical capacity, resulting in slower than expected performance of the configured systems along with the potential for increased dissatisfaction in the overall system performance. The addition of higher numbers of analytical units provides diminishing returns very quickly in this configuration, and provides less and less utilization of the available analytical capacity within the system, further increasing the potential for frustration on the part of the end user.

Examining the overall function and behavior of the system, and looking at the three major delay sources used in this analysis, it is shown there are three key areas for improvement: (1) increasing the linear speed rate of the track system, (2) reducing, or more favorably, eliminating the gate penalty, and (3) minimizing the overall increase of analytical system throughput performance, as it has little effect on the overall system performance when compared with (1) and (2). Increasing the number of analytical systems in the examples discussed herein introduces an overall 8.1 s penalty on the overall throughput because of the required track and devices, with an improvement in performance equivalent to the new analyzer's influence on the average throughput performance of the attached analyzers (for this example, there would be a net zero change in performance as they are all considered to be 16 s, whereas, if the new analyzer was twice as fast, only a 2.66 s increase would be realized, resulting in a reduction in system performance of 5.44 s).

To minimize the impacts and improve the realization of available analytical capacity within interconnected systems, a new ecosystem model may include a series of interconnected sample distribution points of small, high efficiency clusters of systems (ideally 2-3 systems with no gates within them and high speed connections). With such a model, large-scale laboratories will be able to more effectively leverage their available analytical capacity and produce more results in a given period of time than they would otherwise be able to.

Now referring to FIG. 4, block diagram representation of a distributed automation system 400, according to embodiments, is shown. The system 400 includes a plurality of interconnected modules (or analyzers) 101*a* and 101*b*. Two modules are shown for simplicity, but additional modules may be added in accordance with embodiments herein.

An automation track with cover 410 is positioned alongside and connected to the plurality of interconnected modules 101. A plurality of carriers 420 move along track with cover 410. Shown are carriers 420a and 420b, with respective carrier identifiers (e.g., barcodes) 422a and 422b. The carriers 420a and 420b transport and deliver one or more vessels 430, each containing a respective sample, between the plurality of interconnected modules 101a and 101b. Shown in FIG. 4 is vessel 430a with vessel identifier 432a on carrier 420a, and vessel 430b with vessel identifier 432b on carrier 420b. Additional carriers 420 and vessels 430 may be incorporated in the system 400. In an embodiment, a carrier 420 may include a plurality of slots or spaces for holding respective vessels 430; while in another embodiment, a carrier 420 may include space for a single vessel 430. The system 400 is not limited to any particular type of carrier.

An acquisition point (A.P.) 440 is located at a portion of the automation track with cover 410 for acquisition of an identification of each of the vessels 430 and each of the carriers 420 by a reader (R) 442, such as a barcode reader for reading barcodes.

Also included in the distributed automation system 400 is a processor 450 which communicates (either wirelessly or through a wired connection) with the acquisition point 440 and the reader 442, with the modules 101a and 101b, as well as with the track and cover 410. The processor 450 is configured to monitor the identification and a location of each of the vessels 430 and each of the carriers 420 and to detect if the track with cover 410 is breached, as described in detail below.

Figure 5:
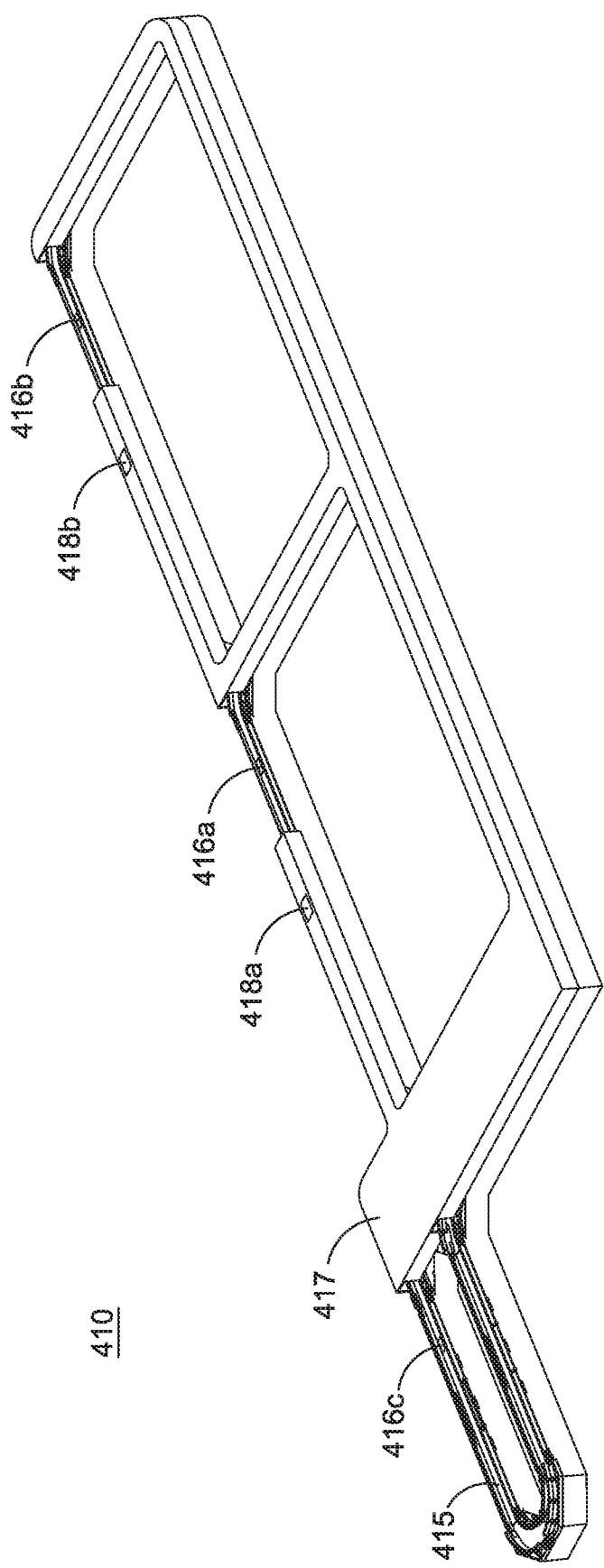
FIG. 5 is a diagram illustrating an exemplary track and cover which may be used with embodiments provided herein.

Now turning to FIG. 5, shown is an exemplary track with cover 410, which may be used with embodiments provided herein. The track portion is denoted 415 and the cover portion is 417. On the track 415 are various track sensors 416a, 416b, and 416c. Various cover sensors 418a, 418b are included on or embedded with portions of the cover 417. Of course, fewer or additional track sensors 416 and cover sensors 418 may be incorporated.

According to an embodiment, the track sensors 416 are positional (e.g., Hall-effect) sensors embedded in or otherwise attached to the track 415 to monitor the position of the various carriers 420. The track sensors 416 may operate with high positional accuracy and send a signal to the processor 450 upon sensing of a carrier 420.

In an embodiment, the cover sensors 418 are on/off sensors, and send a signal to the processor 450 if a portion of the cover 417 corresponding to a particular cover sensor 418 is opened.

In an embodiment, the cover 417 may be a continuous cover set over all areas of the track 415 of travel and destinations for the carriers 420. In another embodiment, the cover 417 may cover a majority portion of the track 415, such as shown in FIG. 5. In yet another embodiment, the cover 417 may cover other portions of the track 415, where those portions are necessary for determining if the cover 417 is breached.

Figure 6:
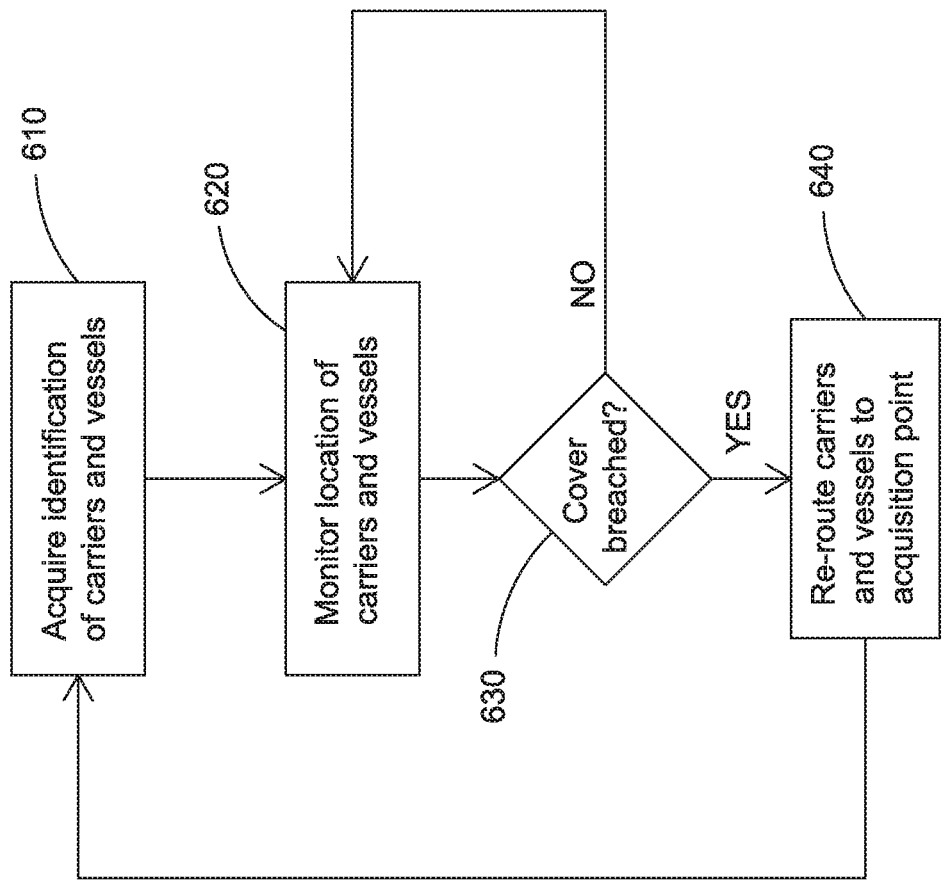
FIG. 6 is a flowchart illustrating a method of utilizing a distributed automation system for use in an in vitro diagnostics (IVD) environment, according to embodiments.

FIG. 6 is a flowchart 600 illustrating a method of utilizing a distributed automation system for use in an in vitro diagnostics (IVD) environment, according to embodiments.

At 610, an acquisition step occurs including acquiring identification of carriers 420 and vessels 430. This acquisition step occurs at the single acquisition point 440 with the reader 442. The acquired information is sent to the processor 450.

At 620, through the various track sensors 416, the location of the carriers 420 and the vessels 430 is monitored.

At 630, a determination is made as to whether a portion of the cover 417 is breached. This determination may be through receipt of a signal sent from one of the cover sensors 418 to the processor 450, indicating a portion of the cover 417 is opened. If no such signal is received, the monitoring of the position (i.e., location) of the carriers 420 and the vessels 430 continues.

At 640, following a signal that the cover 417 is breached, the system, via a signal from the processor 450, reroutes the carriers 420 and the vessels 430 to the acquisition point 440, and the process repeats with acquiring identification of carriers 420 and vessels 430.

Although embodiments are described with respect to a clinical analyzer module, the invention is not so limited. The system may be extended by one of ordinary skill in the art to other types of modules, systems, and/or environments.

Figure 7:
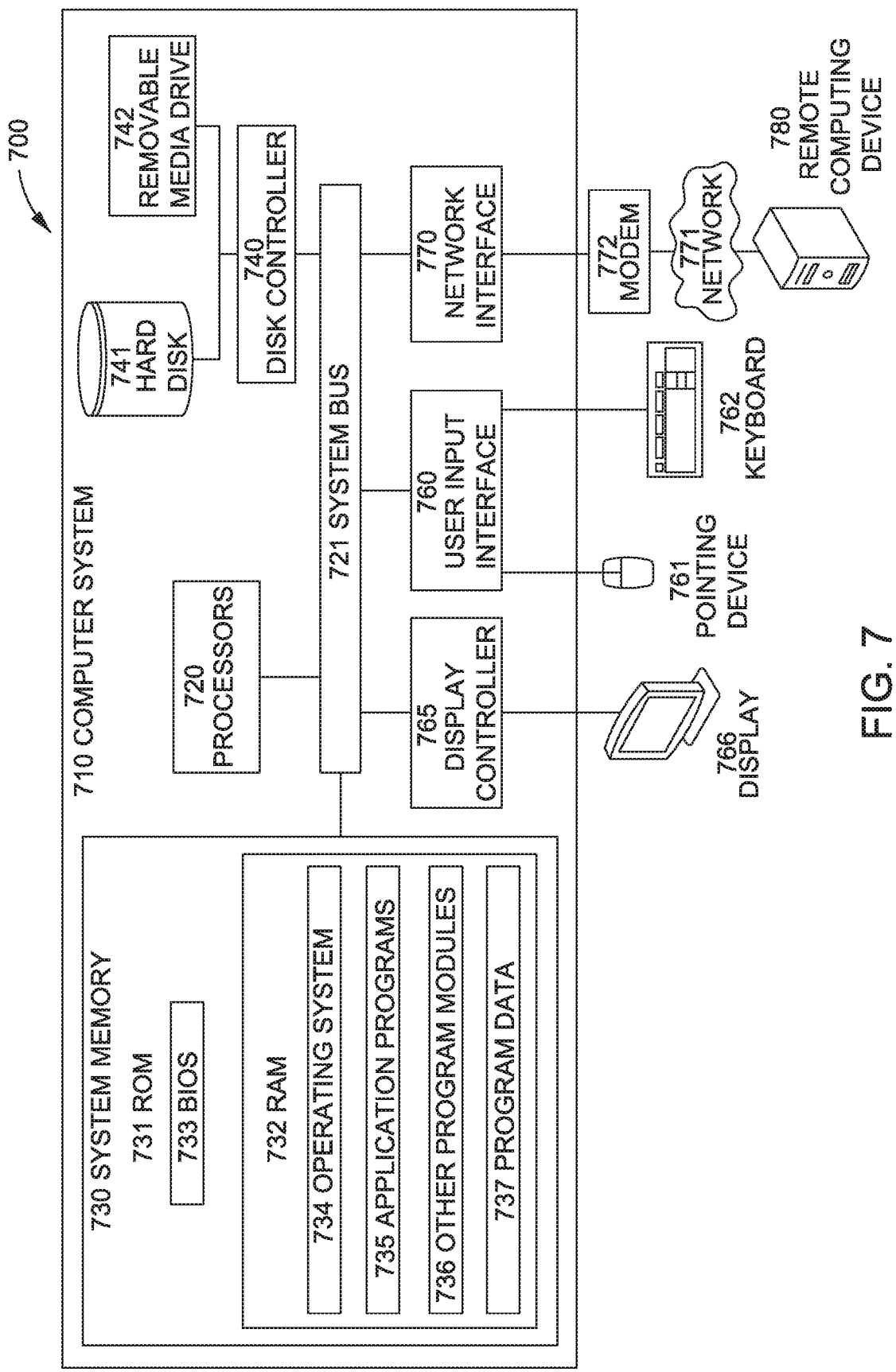
FIG. 7 is an exemplary computing environment in which embodiments disclosed herein may be implemented.

FIG. 7 illustrates an exemplary computing environment 700 within which embodiments of the invention may be implemented. Computing environment 700 may include computer system 710, which is one example of a computing system upon which embodiments of the invention may be implemented. Computers and computing environments, such as computer system 710 and computing environment 700, are known to those of skill in the art and thus are described briefly here.

As shown in FIG. 7, the computer system 710 may include a communication mechanism such as a bus 721 or other communication mechanism for communicating information within the computer system 710. The system computer 710 further includes one or more processors 720 coupled with the system bus 721 for processing the information. The processors 720 may include one or more central processing units (CPUs), graphical processing units (GPUs), or any other processor known in the art.

The computer system 710 also includes a system memory 730 coupled to the bus 721 for storing information and instructions to be executed by processors 720. The system memory 730 may include computer readable storage media in the form of volatile and/or nonvolatile memory, such as read only memory (ROM) 731 and/or random access memory (RAM) 732. The system memory RAM 732 may include other dynamic storage device(s) (e.g., dynamic RAM, static RAM, and synchronous DRAM). The system memory ROM 731 may include other static storage device(s) (e.g., programmable ROM, erasable PROM, and electrically erasable PROM). In addition, the system memory 730 may be used for storing temporary variables or other intermediate information during the execution of instructions by the processors 720. A basic input/output system 733 (BIOS) containing the basic routines that help to transfer information between elements within computer system 710, such as during start-up, may be stored in ROM 731. RAM 732 may contain data and/or program modules that are immediately accessible to and/or presently being operated on by the processors 720. System memory 730 may additionally include, for example, operating system 734, application programs 735, other program modules 736 and program data 737.

The computer system 710 also includes a disk controller 740 coupled to the bus 721 to control one or more storage devices for storing information and instructions, such as a magnetic hard disk 741 and a removable media drive 742 (e.g., floppy disk drive, compact disc drive, tape drive, and/or solid state drive). The storage devices may be added to the computer system 710 using an appropriate device interface (e.g., a small computer system interface (SCSI), integrated device electronics (IDE), Universal Serial Bus (USB), or FireWire).

The computer system 710 may also include a display controller 765 coupled to the system bus 721 to control a display or monitor 766, such as a cathode ray tube (CRT) or liquid crystal display (LCD), for displaying information to a computer user. The computer system 710 includes a user input interface 760 and one or more input devices, such as a keyboard 762 and a pointing device 761, for interacting with a computer user and providing information to the processors 720. The pointing device 761, for example, may be a mouse, a trackball, or a pointing stick for communicating direction information and command selections to the processors 720 and for controlling cursor movement on the display 766. The display 766 may provide a touch screen interface which allows input to supplement or replace the communication of direction information and command selections by the pointing device 761.

The computer system 710 may perform a portion or all of the processing steps of embodiments of the invention in response to the processors 720 executing one or more sequences of one or more instructions contained in a memory, such as the system memory 730. Such instructions may be read into the system memory 730 from another computer readable medium, such as a hard disk 741 or a removable media drive 742. The hard disk 741 may contain one or more datastores and data files used by embodiments of the present invention. Datastore contents and data files may be encrypted to improve security. The processors 720 may also be employed in a multi-processing arrangement to execute the one or more sequences of instructions contained in system memory 730. In alternative embodiments, hard-wired circuitry may be used in place of or in combination with software instructions. Thus, embodiments are not limited to any specific combination of hardware circuitry and software.

As stated above, the computer system 710 may include at least one computer readable medium or memory for holding instructions programmed according to embodiments provided herein and for containing data structures, tables, records, or other data described herein. The term "computer readable medium" as used herein refers to any medium that participates in providing instructions to the processors 720 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 741 or removable media drive 742. Non-limiting examples of volatile media include dynamic memory, such as system memory 730. Non-limiting examples of transmission media include coaxial cables, copper wire, and fiber optics, including the wires that make up the bus 721. Transmission media may also take the form of acoustic or light waves, such as those generated during radio wave and infrared data communications.

The computing environment 700 may further include the computer system 710 operating in a networked environment using logical connections to one or more remote computers, such as a remote computing device 780. Remote computing device 780 may be a personal computer (laptop or desktop), a mobile device, a server, a router, a network PC, a peer device or other common network node, and typically includes many or all of the elements described above relative to computer system 710. When used in a networking environment, computer system 710 may include modem 772 for establishing communications over a network 771, such as the Internet. Modem 772 may be connected to system bus 721 via user network interface 770, or via another appropriate mechanism.

Network 771 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 710 and other computers (e.g., remote computing device 780). The network 771 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 771.

As described herein, the various systems, subsystems, agents, managers and processes can be implemented using hardware components, software components and/or combinations thereof.

Although the present invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

We claim:

1. A distributed automation system for use in an in vitro diagnostics (IVD) environment comprising a plurality of carriers, each of the carriers comprising a label with a unique identification code and containing one or more vessels, each vessel comprising a label with a unique identification code and containing a respective sample, the system comprising:
    a plurality of interconnected modules;
    an automation track alongside and connected to the plurality of interconnected modules, along which the plurality of carriers move, the plurality of carriers transporting and delivering one or more vessels, each containing a respective sample, between the plurality of interconnected modules, wherein the automation track forms at least one loop to a single acquisition point;
    a barcode reader located at the single acquisition point at a portion of the automation track for acquiring an identification of each of the vessels and each of the carriers by the barcode reader;
    a cover set over areas of travel and destinations for the samples; and
    a processor configured to monitor the identification and a location of each of the vessels and each of the carriers and to detect if receive a signal indicating the cover is breached.

2. The system of claim 1, wherein, the processor is configured to, in response to receiving a signal indicating the cover is breached, reroute the respective carriers and vessels to the single acquisition point.

3. The system of claim 2, further comprising a plurality of cover sensors, each associated with a portion of the cover and configured to send a signal to the processor upon the respective portion of the cover being breached.

4. The system of claim 2, wherein, upon the respective carriers and vessels being rerouted to the single acquisition point, a reacquisition of the identification of each of the vessels and each of the carriers is obtained.

5. The system of claim 1, further comprising a plurality of track sensors embedded in the track, the track sensors configured to sense a position of the plurality of carriers and communicate the sensed position to the processor.

6. The system of claim 1, wherein the barcode reader reads each of the unique identification codes for the acquiring of the identification of each of the vessels and each of the carriers.

7. The system of claim 1, wherein a throughput of the system is based on delays incurred at each of the plurality of interconnected modules and along track segments of the automation track.

8. The system of claim 1, wherein the system further comprises a series of interconnected sample distribution points of clusters of additional systems.

9. The system of claim 1, wherein the cover is (i) set over all areas of the track, (ii) set over a majority portion of the track, or (iii) set over a minority portion of the track.

10. A method of utilizing a distributed automation system for use in an in vitro diagnostics (IVD) environment, the method comprising:
   providing a plurality of interconnected modules;
   providing a plurality of carriers, wherein each of the carriers comprises one or more vessels, wherein each vessel comprises a respective sample;
   providing an automation track connected to and alongside the plurality of interconnected modules, along which a carriers move, the plurality of carriers transporting and delivering one or more vessels, each containing a respective sample, between the plurality of interconnected modules, wherein the automation track forms at least one loop to a single acquisition point;
   providing a barcode reader, at the single acquisition point at a portion of the automation track;
   providing a cover set over areas of travel and destinations for the samples;
   acquiring, at the single acquisition point at a portion of the automation track, an identification of each of the vessels and each of the carriers by the barcode reader;
   monitoring, by the processor, the identification and a location of each of the vessels and each of the carriers; and
   receiving, by the processor, a signal indicating the cover is breached.

11. The method of claim 10, further comprising, when a signal indicating the cover is breached is received, rerouting, by the processor, respective carriers and vessels to the single acquisition point.

12. The method of claim 11, wherein a plurality of cover sensors are provided in the cover, each associated with a portion of the cover and configured to send a signal to the processor upon the respective portion of the cover being breached.

13. The method of claim 11, further comprising, upon the respective carriers and vessels being rerouted to the single acquisition point, reacquiring the identification of each of the vessels and each of the carriers.

14. The method of claim 10, wherein a plurality of track sensors are embedded in the track, the track sensors configured to sense a position of the plurality of carriers and communicate the sensed position to the processor.

15. The method of claim 10, wherein each of the plurality of carriers and the vessels comprise a label assigning each a unique identification code.

16. The method of claim 15, wherein the barcode reader reads each of the unique identification codes for the acquiring of the identification of each of the vessels and each of the carriers.

17. The method of claim 10, wherein a throughput of the distributed automation system is based on delays incurred at each of the plurality of interconnected modules and along track segments of the automation track.

18. The method of claim 10, further comprising providing a series of interconnected sample distribution points of clusters of additional systems.

19. The method of claim 10, wherein the cover is (i) set over all areas of the track, (ii) set over a majority portion of the track, or (iii) set over a minority portion of the track.

* * * * *